United States Patent [19]

Velenyi et al.

[11] 4,299,991
[45] Nov. 10, 1981

[54] FORMATION OF HYDROPEROXIDES

[75] Inventors: Louis J. Velenyi, Lyndhurst; Curtie E. Uebele, Bedford; Serge R. Dolhyj, Parma, all of Ohio

[73] Assignee: The Standard Oil Company, Cleveland, Ohio

[21] Appl. No.: 108,079

[22] Filed: Dec. 28, 1979

[51] Int. Cl.$^3$ ........................................... C07C 179/035
[52] U.S. Cl. .................................... 568/573; 568/565; 568/574
[58] Field of Search ................. 568/573, 574, 575, 565

[56] References Cited

U.S. PATENT DOCUMENTS

| 2,734,086 | 2/1956 | Goppel et al. | 568/573 |
| 3,845,140 | 10/1974 | Brownstein et al. | 568/575 |
| 4,013,725 | 3/1977 | Yonemitsu et al. | 568/575 |
| 4,182,909 | 1/1980 | Angstadt et al. | 568/574 |

FOREIGN PATENT DOCUMENTS

| 558506 | 6/1958 | Canada | 568/573 |
| 1313908 | 4/1973 | United Kingdom | 568/574 R |
| 1395367 | 5/1975 | United Kingdom | 568/575 |

OTHER PUBLICATIONS

Nakayama et al., "Journal of Polymer Science"; Part A-1, vol. 5, 1619–1633, (1967).

Primary Examiner—Werren B. Lone
Attorney, Agent, or Firm—Gary R. Plotecher; Herbert D. Knudsen; Larry W. Evans

[57] ABSTRACT

Hydroperoxidizable hydrocarbons are hydroperoxidized by contacting them at hydroperoxidation conditions in the presence of a catalyst comprising a polymer containing maleimide linkages. For example, cumyl hydroperoxide can be produced by contacting cumene and oxygen with a catalyst comprising polymaleimide.

4 Claims, No Drawings

FORMATION OF HYDROPEROXIDES

BACKGROUND OF THE INVENTION

This invention relates to a novel process for hydroperoxidizing a hydroperoxidizable hydrocarbon to produce a hydrocarbon product containing the same number of carbon and hydrogen atoms and two additional oxygen atoms.

The hydroperoxidation of organic compounds is generally well known. This process can be illustrated by the following general equation:

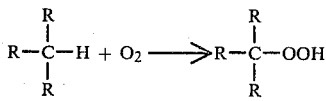

wherein R is a suitable substituent.

Organic compounds are commercially hydroperoxidized by contacting the compound to be hydroperoxidized with oxygen at an elevated temperature, preferably in the presence of a catalyst. However, according to many of these prior art processes, the products are obtained at relatively low levels of conversion and selectivity. Accordingly, it is an object of the present invention to provide an improved process for the catalytic hydroperoxidation of organic compounds, wherein the desired product compounds are produced in higher yields and with higher selectivities than processes known in the prior art.

SUMMARY OF THE INVENTION

These and other objects are accomplished by the present invention in accordance with which hydroperoxidizable hydrocarbons are hydroperoxidized by contacting the hydrocarbon with oxygen in the presence of a catalyst comprising a polymer containing maleimide linkages.

More specifically, the present invention provides a process for contacting a tertiary alkyl aromatic and oxygen in the presence of a polymaleimide catalyst to form the corresponding hydroperoxide.

DETAILED DESCRIPTION

Reactants

The hydroperoxidizable hydrocarbon can, in general, be any organic compound having 1 to 30 carbon atoms per molecule and containing at least 1 carbon atom having a hydrogen atom attached thereto. Particularly suitable hydroperoxidizable hydrocarbons are tertiary alkanes, tertiary aryl-alkanes and tertiary cyclo-alkanes containing 3 to 30 carbon atoms per molecule.

Specific examples of suitable hydrocarbons are: isobutane, isopentane, 2-methyl pentane, 3-methyl hexane, 2,3-dimethyl hexane, 4-methyl heptane, 4-n-propyl heptane, 3-tertiary butyl-hexane, 2-methyl decane, 2,6-dimethyl-3-isopropyl heptane, 2,11-dimethyl dodecane, 2-methyl-heptadecane, 7-isopropyl hexadecane, 4-n-propyl-nonadecane, cyclohexylbenzene, cyclopropane, propylcyclopropane, 1-methyl 2(2-methyl propyl) cyclopropyl, cyclobutane, 1,2-dimethyl cyclobutane, 1,2-diisopropyl cyclobutane, cyclopentane, ethyl cyclopentane, cyclohexane, 1,2,4-trimethyl cyclohexane, propylcycloheptane, cyclooctane, methylcyclooctane, cycloundecane, cyclododecane, cyclooctadecane, cyclopentylcyclopentane, cyclopentylcyclohexylmethane, bicyclohexane, ethylbenzene, cumene, O-cymene, 2-ethyl naphthalene, 2-ethyl-6-methyl naphthalene and mixtures thereof. A particularly preferred group of hydrocarbons for use in the present process are tertiary alkyl aromatics such as ethylbenzene and cumene.

The hydroperoxidizable hydrocarbon may contain more than 1 secondary and/or tertiary carbon. Such highly branched and substituted hydrocarbons are generally suitable for the present process, however, it should be borne in mind that their presence can result in a great profusion of products since the number of principle active sites is increased. It should be expected that the use of exotic or complex hydrocarbon starting materials will probably give lower selectivities to the desired hydroperoxides.

Any source of molecular oxygen can be employed in the instant process. Air is the preferred source. Although the molar ratio of oxygen to hydroperoxidizable hydrocarbon is not critical to the instant process, the minimum ratio of oxygen to hydrocarbon should be 1:1. A large excess of oxygen is preferred.

Any material which is inert to the reactants, catalysts and products of the inventive reaction may also be included within the reaction system as a diluent. For example, steam, nitrogen gas, inert gases, carbon dioxide, paraffins and/or benzene could be added to the reaction system, if desired.

Process Conditions

In carrying out the inventive process, the hydroperoxidizable hydrocarbon is contacted with oxygen and a catalyst as described below for effecting the hydroperoxidation process. This reaction can be accomplished both in a batch mode and continuously. The instant reaction is carried out in the liquid phase at pressures of atmospheric up to about 1,000 psi. Reaction temperatures are normally maintained between 60° C. and 200° C., more preferably between 110° C. and 150° C. It may be preferable to use a high initial temperature, i.e. 160° C. to 170° C., which will allow the rapid build-up of initiator, i.e. hydroperoxide. However, once the reaction is initiated the temperature is reduced to normal operating levels. Temperatures higher than 170° C. should not be employed after the reaction has been initiated since the possibility of further oxidation of the hydroperoxide is enhanced.

Advantageously, small amounts of an initiator can be added to the instant process. Preferably, this initiator is some of the hydroperoxide product to be produced. Other initiators such as alpha-methyl benzyl hydroperoxide, alpha-methyl-p-methylbenzyl hydroperoxide, alpha-methyl-n-propyl-p-xylene dihydroperoxide, ethylacetoacetate, phenylacetone, acetylacetone and the like may also be used.

The reaction is generally complete in from 1 to 10 hours, depending upon the amount of substrate employed. It may be preferable to terminate the reaction prior to completion in order to avoid excessive decomposition of the hydroperoxide.

Catalysts

The catalysts employed in this reaction comprise a polymer-containing maleimide linkages. These maleimide linkages can be represented by the following formula:

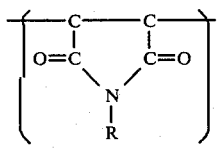

wherein R is selected from the group consisting of aryl, alkyl, H, Group IA, IIA, copper, thallium, lanthanum and cerium. If R is multi-valent, then it may link to other maleimide linkages to satisfy the valence requirement.

The polymers containing these maleimide linkages are well known in the art and are described in detail in the *Journal of Polymer Science: Part A*-1, Vol. 5, pp. 1619-1633 (1967) and Ibid., Vol. 4, pp. 1121-1134 (1966).

Comonomers which are usable in the instant catalyst with the maleimide linkages are selected from a wide variety of material which are compatible with the reactants and products. Preferred comonomers are styrene, ethylene and propylene.

Generally, the hydrocarbon/catalyst ratio will be about 1-10/1 by weight. This ratio will vary depending upon the hydroperoxidizable hydrocarbon and the particular catalyst used. Preferably, this ratio will be about 2 to 1.

The hydroperoxides obtained by the process of this invention are highly useful in various important commercial applications. Thus, for example, when cumene is oxidized in accordance with the present invention, there is formed alpha-cumyl hydroperoxide which, when reacted with an acid such as sulfuric acid, can be converted to industrially useful phenol and acetone in accordance with known reactions.

SPECIFIC EMBODIMENTS

In order to more thoroughly describe the present invention, the following working examples are presented. In each of these examples the following definitions are used:

$$\% \text{ PPC} = \frac{\text{Gms. Carb. in Reactant Conv. to Prod.}}{\text{Gms. Carb. in Reactant Fed}} \times 100$$

$$\% \text{ Select.} = \frac{\text{Gms. Carb. in Reactant Conv. to Prod.}}{\text{Gms. Carb. in Reactant Reacted}} \times 100$$

EXAMPLE 1

45 gms. of cumene were placed in a three-neck flask fitted with a condenser, thermometer and a gas inlet tube. An initiator comprising 0.5 gms. of cumene hydroperoxide was added to the flask. Next, 0.5 gms. of polymaleimide were added to the flask. The resultant mixture was heated to 117° C. with constant stirring while oxygen was bubbled through the liquid. After 4½ hours the reaction was stopped and the hydroperoxide content was analyzed. 25% PPC cumene hydroperoxide was formed with a selectivity of 94%.

EXAMPLE 2

45 gms. of cyclohexylbenzene was placed in a three-neck flask fitted with a condenser, thermometer and a gas inlet tube. An initiator comprising 0.5 gms. of cumene hydroperoxide was added to the flask. Next, 0.5 gms. of polymaleimide was added to the flask. The resultant mixture was heated to 115° C. with constant stirring while oxygen was bubbled through the liquid. After 4½ hours, the reaction was stopped and the hydroperoxide content was analyzed. It was found that 5.7% PPC cyclohexylbenzene hydroperoxide was formed with a 89.1% selectivity.

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A process for producing hydroperoxides comprising contacting at a temperature of about 60° C. to about 200° C. and a pressure of about 1 atmosphere to about 1000 psi a hydroperoxidizable hydrocarbon selected from the group consisting of tertiary alkanes, tertiary aryl-alkanes and tertiary cyclo-alkanes containing up to 30 carbon atoms per molecule with oxygen in the presence of a polymaleimide catalyst.

2. The process of claim 1 wherein the hydroperoxidizable hydrocarbon is a tertiary alkyl aromatic.

3. The process of claim 2 wherein the hydroperoxidizable hydrocarbon is ethylbenzene.

4. The process of claim 2 wherein the hydroperoxidizable hydrocarbon is cumene.

* * * * *